United States Patent
Lu et al.

(10) Patent No.: US 11,048,939 B2
(45) Date of Patent: Jun. 29, 2021

(54) HEALTH TRENDS IDENTIFICATION

(71) Applicant: International Business Machines Corporation, Armonk, NY (US)

(72) Inventors: Fang Lu, Billerica, MA (US); Italo Buleje, Orlando, FL (US); Jingwei Yang, Cambridge, MA (US); Piyush Madan, Boston, MA (US); Rachita Chandra, Cambridge, MA (US); Shilpa N. Mahatma, Chappaqua, NY (US); Sundar Saranathan, Framingham, MA (US)

(73) Assignee: International Business Machines Corporation, Armonk, NY (US)

( * ) Notice: Subject to any disclaimer, the term of this patent is extended or adjusted under 35 U.S.C. 154(b) by 228 days.

(21) Appl. No.: 16/124,439

(22) Filed: Sep. 7, 2018

(65) Prior Publication Data
US 2020/0082169 A1    Mar. 12, 2020

(51) Int. Cl.
*G06K 9/00* (2006.01)
*G08B 21/18* (2006.01)
*G06K 9/62* (2006.01)
*G16H 20/60* (2018.01)

(52) U.S. Cl.
CPC ....... *G06K 9/00664* (2013.01); *G06K 9/6201* (2013.01); *G08B 21/182* (2013.01); *G16H 20/60* (2018.01)

(58) Field of Classification Search
CPC ............. G06K 9/00664; G06K 9/6201; G08B 21/182; G08B 21/0476; G16H 20/60

USPC ................................................. 382/100, 103
See application file for complete search history.

(56) References Cited

U.S. PATENT DOCUMENTS

| | | | |
|---|---|---|---|
| 9,364,106 B1 | 6/2016 | Ortiz | |
| 9,892,656 B2 | 2/2018 | Ortiz et al. | |
| 9,928,651 B2 | 3/2018 | Mariappan | |
| 2007/0059672 A1* | 3/2007 | Shaw | G09B 19/0092 434/127 |
| 2015/0228062 A1* | 8/2015 | Joshi | G06Q 50/12 382/110 |
| 2016/0035248 A1* | 2/2016 | Gibbs | G09B 5/02 434/127 |
| 2017/0091420 A1* | 3/2017 | Duggan | G06F 19/324 |
| 2017/0323481 A1* | 11/2017 | Tran | G06F 19/00 |

(Continued)

OTHER PUBLICATIONS

Recapt, "Overview of Consumer Trends in Food Industry," Dec. 2011, 27 pages.

(Continued)

*Primary Examiner* — Andrew M Moyer
(74) *Attorney, Agent, or Firm* — Patterson + Sheridan, LLP

(57) ABSTRACT

Methods and apparatus for identifying health trends via the identification of ambiguous food items via container identification may be provided by: receiving an image captured from a user device that includes a food item; identifying a food container present in the image; identifying a utensil present in the image; determining a cluster of food items from a food recognition database corresponding to the food container and to the utensil; selecting a candidate food item from the cluster based on a confidence score of the candidate food item matching the food item; and adding the candidate food item to a dietary log associated with the user device.

20 Claims, 3 Drawing Sheets

(56) References Cited

U.S. PATENT DOCUMENTS

2018/0149519 A1* 5/2018 Connor ................ G01J 3/0256

OTHER PUBLICATIONS

Anonymously, "Health improvement system using biosensors and food intake patterns," May 9, 2016.
Anonymously, "Method and apparatus for Cognition enabled Discernment Specialist for Restaurant food order," Jan. 19, 2017.

* cited by examiner

HEALTH TRENDS IDENTIFICATION

BACKGROUND

The present invention relates to image recognition, and more specifically, to real-time recognition of food items.

SUMMARY

According to one embodiment of the present invention, a method for health trends identification is provided, comprising: receiving an image captured from a user device that includes a food item; identifying a food container present in the image; identifying a utensil present in the image; determining a cluster of food items from a food recognition database corresponding to the food container and to the utensil; selecting a candidate food item from the cluster based on a confidence score of the candidate food item matching the food item; and adding the candidate food item to a dietary log associated with the user device.

According to another embodiment of the present invention, a system for health trends identification is provided, comprising: a processor; and a memory, including instructions that when executed by the processor enable the processor to: receive an image captured from a user device that includes a food item; identify a food container present in the image; identify a utensil present in the image; determine a cluster of food items from a food recognition database corresponding to the food container and to the utensil; select a candidate food item from the cluster based on a confidence score of the candidate food item matching the food item; and add the candidate food item to a dietary log associated with the user device.

According to a further embodiment of the present invention, a computer program product is provided for health trend tracking, the computer program product comprising: a computer-readable storage medium having computer-readable program code embodied therewith, the computer-readable program code executable by one or more computer processors to: receive an image captured from a user device that includes a food item; identify a food container present in the image; identify a utensil present in the image; determine a cluster of food items from a food recognition database corresponding to the food container and to the utensil; select a candidate food item from the cluster based on a confidence score of the candidate food item matching the food item; and add the candidate food item to a dietary log associated with the user device.

DETAILED DESCRIPTION

Managing and tracking the food and drink that a person consumes can be an important part of improving the care and health of that person. For example, a person may have an allergy, and be unaware that a food item contains an allergen, may be on a restricted diet and only be allowed to consume certain foods, may be on a watch for food triggers to medical conditions, etc. A person may self-report what has been consumed, for example in a journal, but journals rely on accurate record keeping, knowledge on the part of the reporter of the food item consumed, and are often inaccurate in the quantity consumed. Computer diet tracking has, heretofore, been unreliable in aiding diet reporting, as complex mixtures of food items may pose difficulties in identifying an item being consumed by a particular person. Additionally, a food item may obscure or mix several ingredients together that may make image analysis of the food item itself unreliable. For example, a sandwich, wrap, curry, soup or other dish may mix several meats, vegetables, cheeses, starches, sauces, etc., together that may cover one another and prevent the imaging and identification of those ingredients. By focusing on the shape, size, and supporting environmental evidence around a food item, a health tracking system may augment the determination of the food item(s) that are consumed.

As used herein, the term "food item" shall be understood to include comestible and potable substances of any type including meals, beverages, condiments, and spices. For example, water, wines, sodas, juices, teas, sandwiches, fruits, vegetables, salads, breads, grains, fish sauces, hot sauces, mustards, salt crystals, gelatins, puddings, milk shakes, and confections are all non-limiting examples of food items. Food items may include non-edible portions and still be considered food items. For example, rinds, bones, gristle, shells, garnishes, plating decorations, and the like are non-limiting examples of potentially non-edible portions of food items.

By aiding in the identification of food items through the identification of food-related objects and related food items that are present in an image, greater accuracy in identifying food items may be achieved. The functionality of an image processing computing device may thereby be improved for identifying food items that contain mixtures and combinations of food items that obscure other food items, and that cannot be identified through direct image recognition of the food item itself.

Figure 1:
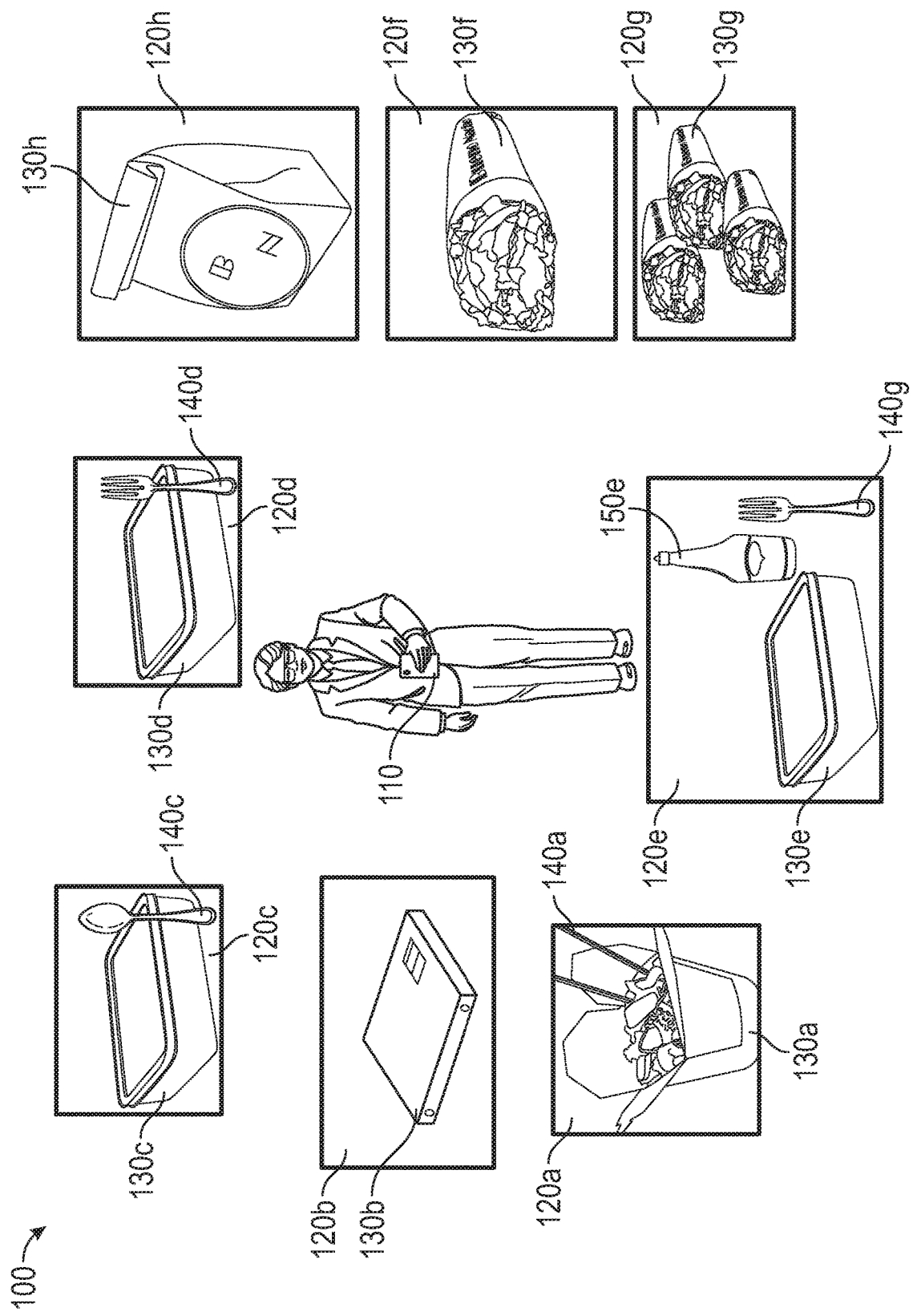
FIG. 1 illustrates an example scenario for health trend tracking, according to aspects of the present disclosure.

With reference now to FIG. 1, an example scenario 100 for health trend tracking is illustrated. A user has equipped a user device 110, which has captured a series of images 120a-h (generally, image 120) of the meals that the user has consumed. In the images 120a-h, various food-related objects have been identified, including containers 130, utensils 140, and secondary containers 150. The images 120 are processed to identify the containers 130, utensils 140, and secondary containers 150 found therein, which are used to identify a food item present in the image 120 in addition to or instead of identifying the food items directly. FIG. 1 presents several images 120, containers 130, utensils 140, and secondary containers 150 as non-limiting examples; other embodiments, using more or fewer images 120 showing different contents are contemplated by the present disclosure.

A machine learning model (stored on either the user device 110 or an external device) may identify a food item via image processing based on an appearance of the food item in the image compared to known category of food items, the presence of various food-related objects, and/or the presence of various related foods. Processing the image 120 to identify the food items themselves may result in an identity of the food item that varies in how specific or rough a match can be found to a known food item. For example, the analysis may result in a very specific identification of the food item (e.g., food item X from restaurant Y) or a very rough identification of the food item (e.g., leftovers of some sort). For food items that include multiple ingredients (e.g., a soup including a mixture of noodles, meats, and vegetables) or are partially obscured by other ingredients (e.g. bread hiding the contents of a sandwich), image processing of the food item alone may be inadequate or produce results that are too rough to be useful (e.g., the food item is identified as a sandwich, but not what type of sandwich). Additionally, meals often include multiple food items, but an image 120 may omit some food items. For example, a user on a diet may submit an image 120 that includes a salad, but omit (intentionally or accidentally) a side of French fries or a soda from the image 120. The presence of supporting items in the image, such as utensils 140 (e.g., none/null, chopsticks, forks, straws, skewers, sporks) that are specific to a particular food type or secondary containers 150 with known associations with a particular food type (e.g., hot sauce packets, salt shakers, soy sauce bottle, drinking vessel) are used to augment the specificity at which the food items are identified.

Secondary containers 150 may refer to containers 130 for different food items in the image 120 that are associated with known food items themselves (e.g., a ketchup packet is associated with ketchup, a cup is associated with soda, a second taco wrapper is associated with a second taco) or may refer to packages for the containers 130 holding the food item (e.g., a paper bag holding a take-out box). Although the images 120 in FIG. 1 show zero to one secondary containers 150, in other embodiments, two or more secondary containers may be included in and analyzed from an image 120.

Image processing to identify the food item may be performed locally (e.g., on the user device 110) and/or remotely (e.g., on a computing device other than the user device 110). In various embodiments, the image processing is performed in batches (e.g., several images 120 for meals consumed throughout the day/week/month/etc. are uploaded/analyzed at one time) or in real-time (e.g., when an image 120 is captured, the image 120 is analyzed). The user device 110 may capture images 120 in response to a command from the user or a third party, on a time schedule (e.g., every 30 seconds, at noon, every 30 seconds starting at noon lasting for one hour), in response to a location signal (e.g., leaving a desk, entering a cafeteria, being located at a geographic coordinate set associated with serving food) or the like.

In various embodiments, the image processing device uses the shape, color, and/or size of the container 130 (or secondary container 150) to help identify the food item in the image 120. In other embodiments, a presence/absence or type of utensil 140 in the image 120 is used to identify the food item in the image 120. For example, a first image 120a shows a first container 130a for takeout food of a plain box, and first utensils 140a of chopsticks, while a second image 120b shows a second container 130b for a takeout food of a plain box, and no utensils. The distinctive shape of the first container 130a may be recognized as a takeout container associated with an Asian restaurant, and the chopsticks, as utensils 140 associated with several Asian foods, may reinforce the determination that the user is consuming Asian food. Similarly, the distinctive shape of the second container 130b and lack of utensils 140 may reinforce the determination that the user is consuming pizza.

In another example, a third image 120c and a fourth image 120d each show an identical third container 130c and fourth container 130d, respectively, but include different utensils 140; the third utensil 140c is a spoon, whereas the fourth utensil 140d is a fork. A spoon may be associated with foods with high liquid contents (e.g., soups, heavily sauced meals), while the utensil 140 may be identified by the shape, color, and/or size, and the presence of absence of a utensil 140 is used is used to help identify the food item in the image 120.

In various embodiments, the image processing device uses the presence or absence of a utensil 140 or secondary container 150 to help identify the food item in the image 120. For example, a fifth container 130e and fifth utensil 140e in the fifth image 120e match the third container 130c and third utensil 140c, but the presence of a fifth secondary container 150e in the fifth image 120e may help differentiate the food items in the two images 120. In one embodiment, if the fifth secondary container 150e is identified as salad dressing, then the food item in the fifth container 130e may be identified as a salad, while the food item in the third container 130c may be less likely to be identified as a salad because no dressing is identified in the third image 120c. In another example, the fifth secondary container 150e may be identified as a wine glass, and the food item identified as a noodle dish, which is refined to an Italian noodle dish rather than a Chinese or Japanese noodle dish, due to a stronger association between wine and Italian cuisine than between wine and Chinese or Japanese cuisine.

In some embodiments, the image processing device analyzes the identified containers 130, utensils 140, and secondary containers 150 for logos or other identifying marks to identify the food item. For example, in the sixth image 120f, seventh image 120g, and eighth image 120h, the corresponding containers 130f-h may include writing, logos, or markings that identify the source of the food item. For example, the bag illustrated on the eighth container 130h has a logo for a fast food chain, which may help identify the food item. The sixth container 130f and the seventh container 130g include a word mark that may be processed for text recognition to identify the food items contained therein. Additionally, the sizes of sixth container 130f and the seventh container 130g may be used in identifying the food items contained therein.

Figure 2:
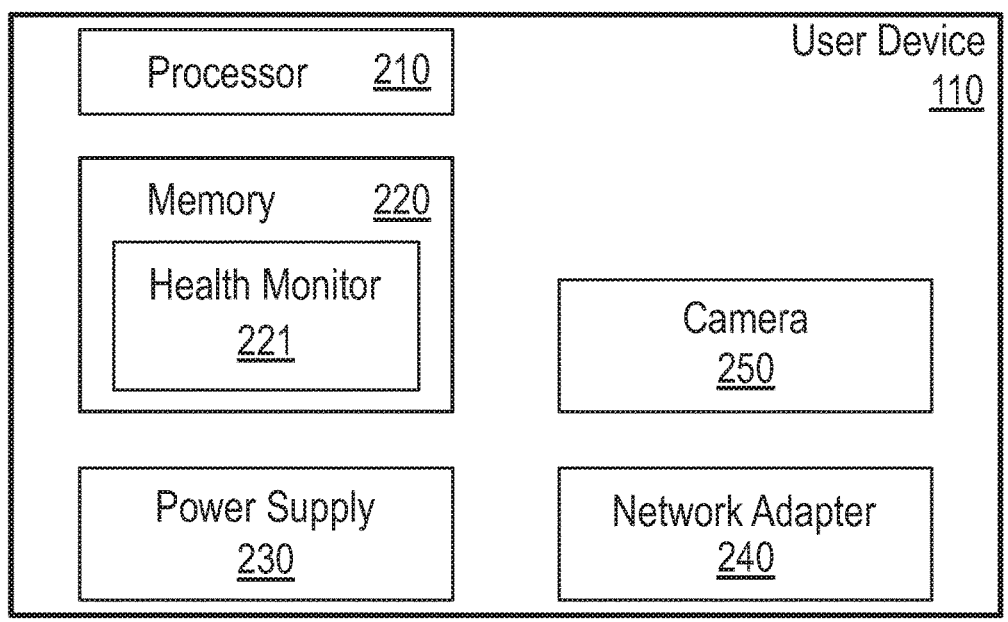
FIG. 2 illustrates details of an example user device, according to aspects of the present disclosure.

FIG. 2 illustrates details of an example user device 110. The internal components of a given user device 110 may vary from those illustrated in FIG. 2, and several instances of each component may be included in a given user device 110. The internal components include a processor 210, a memory 220, a power supply 230, a network adapter 240, and a camera 250. In various embodiments, the user device 110 is a computing device, such as, but not limited to: a smart phone, a tablet, a digital camera, a bodycam, or the like.

The processor 210 and the memory 220 provide computing functionality to the user device 110. The memory 220 may be one or more memory devices, such as, for example, Random Access Memory (RAM), Read Only Memory (ROM), flash memory, or any other type of volatile or non-volatile storage medium that includes instructions that the processor 210 may execute to affect the user device 110. The processor 210, which may be any computer processor capable of performing the functions described herein, executes commands included in the instructions, which may include performing certain tasks in response to signals received via the network adapter 240.

The memory 220 generally includes program code for a health monitor 221 for performing various functions related image processing, diet tracking, and alerting. The health monitor 221 is generally described as various functional "processor executable instructions," "applications," or "modules" within the memory 220, although alternate implementations may have different functions and/or combinations of functions. The health monitor 221 includes the dietary log for the user, which may be periodically uploaded to or shared with an external device. Additionally, the health monitor 221 may include definitions for image processing and identifying various food items and/or food paraphernalia from images 120 captured by the user device 110. In some embodiments, the health monitor 221 includes an image processor to identify various objects in an image 120 for the analysis and identification of food items and the health trends of an associated user. In further aspects, the health monitor 221 may include a machine learning model 321 (discussed in greater detail in regard to FIG. 3).

A dietary log for the eating habits and health trends of the user collects the food items (and nutritional values thereof) consumed by the user over time based on the food items identified from the images 120 supplied by the user. The dietary log may be maintained on the user device 110 and/or an external device for the user to review dietary choices, provide to a healthcare provider (e.g., doctor, dietician, nutritionist, health coach), and for the user device 110 to alert the user of health trends based on the food consumed. For example, an alert is generated when a food item is identified that includes an allergen or has a nutritional value that exceeds a threshold (e.g., salt/sugar/fat content above a threshold; fiber/vitamin/protein content below a threshold), a food consumption trend is identified (e.g., not enough or too much of a given nutrient consumed in aggregate over a period of time according to a trend threshold).

The dietary log may include a dietary plan that indicates various food items that may be forbidden to the user (e.g., for allergies, medication interferences, dietary goals), and may set a dietary plan that the user is to consume (or avoid consuming) certain foods to adhere to. In some embodiments, the dietary log may be input by a user, a doctor, parent, nutritionist or other person into the health monitor 221, and in other embodiments, the health monitor 211 automatically retrieves some or all of the data in the dietary plan from an external device, such as computing device associated with a doctor, parent, nutritionist, etc., that hosts an account or records for the user.

The dietary log maintains a record of the food items identified from the images 120 and the nutritional information associated with those food items. Depending on the specificity of the food item identified, the nutritional information may be specific or rough. For example, when the food item is identified as a category of food (e.g., food from restaurant X, food of cuisine type Y, a drink of size Z), the mean nutritional value for food items belonging to that that category or the nutritional value for most a popular food item in that category may be selected to represent the roughly identified food item. In another example, when the food item is specifically identified (e.g., food from restaurant X, or type Y, and size Z), the nutritional values for the identified food item will be specific to that food item. The nutritional information may be provided by food purveyors (e.g., restaurants, cafeterias, suppliers/producers, grocery stores) or may be based on established nutritional values for ingredients.

The power supply 230 provides electric power to the various components of the user device 110. Various examples of power supplies 230 include batteries (rechargeable and non-rechargeable), Alternating Current to Direct Current (AC/DC) converters, Direct Current to Alternating Current (DC/AC) converters, transformers, capacitors, inductors, and wiring to connect to an external power source.

The network adapter 240 includes hardware for connecting to external devices by wired and/or wireless networks and connections. The network adapter 240 may be in communication with various antennas and wires, and may configure messages to be transmitted or received according to various standards, such as, Wi-Fi, cellular service, Bluetooth, Universal Serial Bus (USB), etc. The network adapter 240 may receive image definitions, dietary restrictions, alerts, and queries (among other data) from an external device, and may send images 120, dietary logs, alerts, and responses to queries (among other data) to an external device.

The camera 250 included in a user device 110 enables the user device 110 to capture images 120 of the environment, which may include food items and/or related paraphernalia (e.g., containers 130, utensils 140). The camera 250 may include image capturing firmware that automatically focuses the camera 250, (de)activates a flash or lighting-correction, tags a captured image 120 with a date/time and/or geographic location, and captures and stores an image 120 in a selected file format. In various embodiments, the camera 250 is activated in response to the user device 110 receiving a command from the user (e.g., via a physical "shutter" button, a software button, a voice command), in response to a timing signal (e.g., every X seconds, at Y time, every X seconds from Y time to Z time), in response to a query from an external device, etc.

Figure 3:
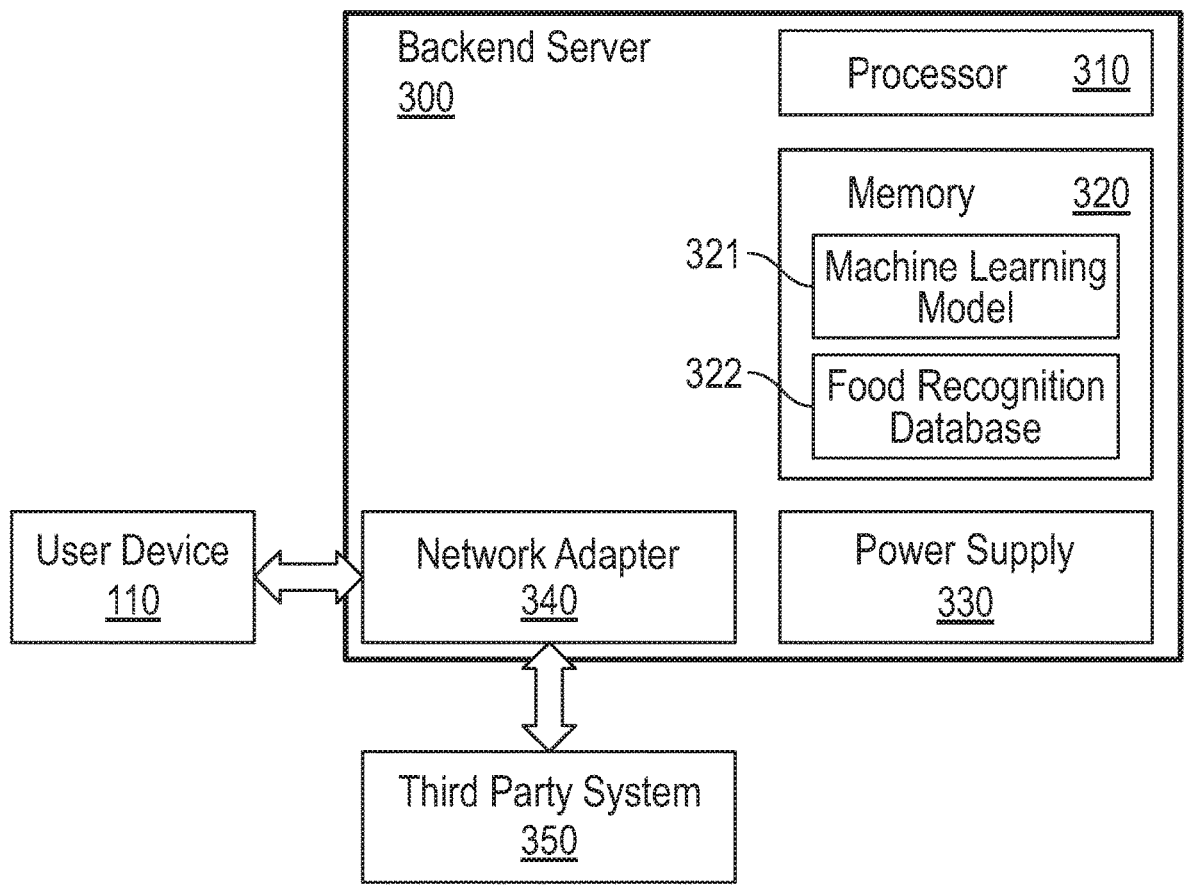
FIG. 3 illustrates details of an example backend server that may be used as an external device for image processing and/or health monitoring in association with a user device, according to aspects of the present disclosure.

FIG. 3 illustrates details of an example backend server 300 that may be used as an external device for image processing and/or health monitoring in association with a user device 110. The backend server 300 includes one or more computing devices to which the user device 110 may upload images 120 and/or the dietary logs to perform processing thereon. The components of a given backend server 300 may vary from those illustrated in FIG. 3, and several instances of each component may be included in a given backend server 300. The internal components include a processor 310, a memory 320, a power supply 330, and a network adapter 340. The backend server 300 may be in communication with a plurality of user devices 110 (associated with different users) and one or more third party device 350, which are computing devices associated with users (e.g., desktop or laptop computers), healthcare offices (e.g., doctors, nutritionists, gyms, insurance providers), which may provide dietary goals, restrictions, and analysis for health monitoring for specified users.

The processor 310 and the memory 320 provide computing functionality to the backend server 300. The memory 320 may be one or more memory devices, such as, for example, Random Access Memory (RAM), Read Only Memory (ROM), flash memory, or any other type of volatile or non-volatile storage medium that includes instructions that the processor 310 may execute to affect the backend server 300. The processor 310, which may be any computer processor capable of performing the functions described herein, executes commands included in the instructions, which may include performing certain tasks in response to signals received via the network adapter 340.

The memory 320 generally includes program code for a machine learning model 321 and a food recognition database 322 for performing various functions related image processing, diet tracking, and alerting. The program code is generally described as various functional "processor executable instructions," "applications," or "modules" within the memory 320, although alternate implementations may have different functions and/or combinations of functions. The machine learning model 321 may include several machine learning models (or profiles) tailored to a specific user or group of users, the dietary logs thereof, and any dietary restrictions set by or for a specific user. The food recognition database 322 includes various rules and cues for identifying various categories of food items from images 120 captured by user devices 110. The rules and cues may include correspondences between utensils 140 and food items, logos/packaging and the providers that use those marks and food items offered by those providers, food items and other associated food items (e.g., condiments to main courses, beverages to foods), portion size information, and the like. In some embodiments, the food recognition database 322 includes an image processor to identify food items and/or food-related objects in images 120 submitted from user devices 110.

In a machine learning approach to identifying food items corresponding to known containers 130, utensils 140, and secondary containers 150, the image processing device (either the user device 110 or the backend server 300) may use several parallel or successive rounds of clustering to help identify a food item included in an image 120. The image processing device may identify a food item as belonging to a likely cluster of foods based on available packaging information (e.g., logos, identifiable color schemes, words on containers 130), size of the items, visible utensils 140, the identities of other food items in the image 120 (via secondary containers 150), knowledge of the user's prior dietary habits, and responses to (optional) queries to the user. For example, an image processing device using a machine learning model 321 may identify an image 120 as including food items from a particular restaurant, which will narrow the field of potential food items that may be included in the image 120 that may be identified by the other evidence in the image 120 (e.g., utensils 140).

The machine learning model 321 may weight various evidence of a food item differently for different users, and may adjust the confidence of an identification based on the user's past history, as indicated in a dietary log. For example, a first user may not use chopsticks for Asian food (preferring to use a fork), and a second user may use chopsticks for Asian food, and the presence or absence of utensils 140 that include chopsticks may be given weight for the identification of food items for the second user, but not the first user. In another example, with a user who frequents a restaurant and orders one given food item, a machine learning model 321 that identifies a container 130 from that restaurant may further identify the image 120 as containing the given food item without further evidence based on past user behavior. In a further example, with a user who frequents a restaurant and varies between ordering one of a select number of food item, a machine learning model 321 that identifies a container 130 from that restaurant may identify the image 120 as containing one of the select number of food items and narrow the determination of which food item of the select number of food items is present in the image 120.

Periodically, or in response to queries, the user may be prompted to identify or confirm the identity of a food item (or food items) in an image 120. In some embodiments, the machine learning model 321 may prompt a query to the user to supply an identity of a food item when a confidence score for the identify for a food item falls below a threshold, or two or more food items satisfy a confidence threshold; when the a machine learning model 321 is unsure of the food item being consumed, the user may be requested to identify the food item. A machine learning model 321 may apply the user-supplied feedback to improve future identifications of food items (e.g., learning the user's eating habits).

The machine learning model 321, in conjunction with the food recognition database 322, may define various clusters of food items that are associated with various food-related objects. For example, a cluster of food items associated with a container 130 having a company logo may include the food items served by a given restaurant associated with that logo. In another example, a cluster of food items associated with a utensil 140 may include the various cuisine consumed with that utensil 140. Two or more clusters may overlap, which the machine learning model 321 uses to reduce the candidate set of food items from the food recognition database 322 to narrow the selection and identification of a food item from the image 120. For example, a restaurant may serve various sandwiches (with no utensil 140) as well as sodas and milkshakes (with a straw utensil 140). The machine learning model 321 may identify a first cluster of food items based on the container 130 (e.g., the food items served by that restaurant), and a second cluster of food items based on the presence of the straw-type utensil 140 (e.g., drinks). By overlaying the two clusters from the food recognition database 322, the machine learning model 321 may be refine the set of candidate food items to the intersection of the two clusters (e.g., drinks served by the identified restaurant).

Additionally, the food recognition database 322 includes the nutritional profiles for various categories of food and specific food items. Depending on the level of specificity at which a food item is identified, a corresponding specificity of nutritional profile is returned by the food recognition database 322. For example, if the level of specificity for the food item only returns a restaurant of origin, the food recognition database 322 may return an average nutritional profile for that restaurant (e.g., the mean or popularity-weighted mean nutritional values for foods served by the restaurant), while if a specific food item from that restaurant is identified, the food recognition database 322 may return a nutritional profile associated with the specifically identified food items. The machine learning model 321 may inform the selection or weighting of the nutritional profile based on a machine learning model 321 of the user's preferences. For example, if a user has a frequently ordered a given food item at a given restaurant, and if only the restaurant can be identified from the image 120, the nutritional profile assigned in the dietary log based on the image 120 may be weighted according to the user's past orders of the frequently ordered food item.

The machine learning models 321 may specify various rules for when to generate alerts based on the observed dietary patterns of the user. Alerts may be generated in response to positive, neutral and negative observations of the user's eating habits. For example, after identifying a food item in an image 120 as a healthy choice, or identifying that the user has achieved a daily goal for nutritional intake (e.g., at least 15 g of fiber daily), an alert may be generated and transmitted to the user device 110 or a third party device 350. In another example, in response to identifying that a food item likely contains an allergen or excessive nutrients of an avoided categories (e.g., sugars, fats, salt beyond a predefined value), an alert may be generated and transmitted to the user device 110 or a third party device 350. In a further example, in response to not receiving an image 120 of a food item within a timespan associated with meals, in response to an update to the dietary goals for the user, in response to receiving a locational update corresponding with a restaurant/kitchen/etc., an alert or query may be sent to the user device 110 requesting an image 120 to be captured.

The power supply 330 provides electric power to the various components of the backend server 300. Various examples of power supplies 330 include batteries (rechargeable and non-rechargeable), Alternating Current to Direct Current (AC/DC) converters, Direct Current to Alternating Current (DC/AC) converters, transformers, capacitors, inductors, and wiring to connect to an external power source.

The network adapter 340 includes hardware for connecting to external devices (e.g., user devices 110 and/or third party devices 350) by wired and/or wireless networks and connections. The network adapter 340 may be in communication with various antennas and wires, and may configure messages and data to be transmitted or received according to various standards, such as, Wi-Fi, cellular service, Bluetooth, Universal Serial Bus (USB), etc. The network adapter 340 may receive image definitions, dietary restrictions, alerts, and responses queries (among other data) from an external device, and may send dietary logs, alerts, and queries (among other data) to an external device.

Figure 4:
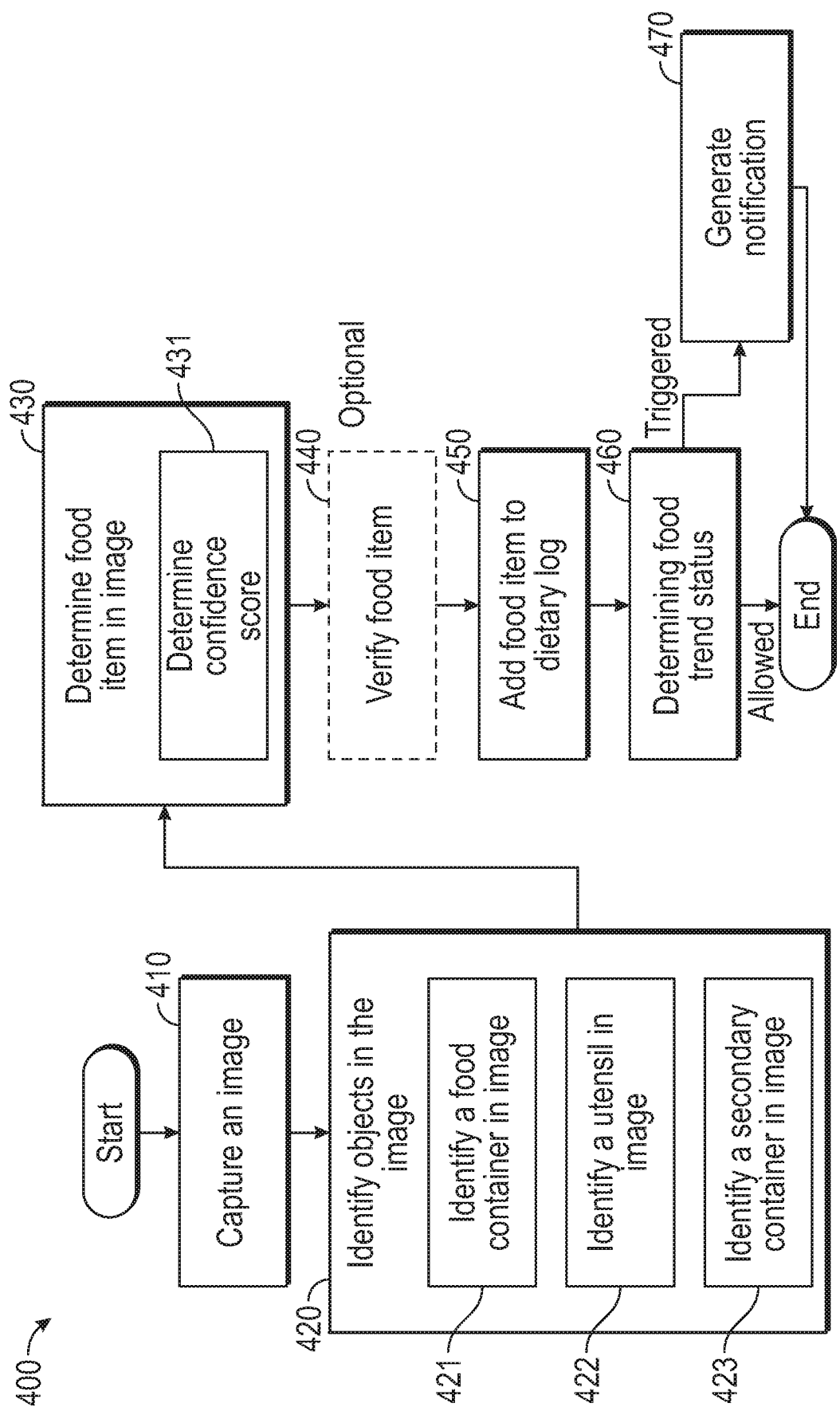
FIG. 4 is a flowchart of an example method for health trends identification, according to aspects of the present disclosure.

FIG. 4 is a flowchart of an example method 400 of health trends identification. Method 400 begins at block 410, where a user device 110 captures an image 120. At block 420, the user device 110 or backend server 300 analyzes the image 120 to identify objects related to food items in the image 120. In some embodiments, the user device 110 performs block 420 locally via health monitor 221, while in other embodiments, the user device 110 transmits the image 120 captured in block 410 to a backend server 300 to process the image 120 per block 420 via a machine learning model 321. In various embodiments, the user device 110 or backend server 300 perform block 420 in response to a query to the food recognition database 322 returning a "no-match" result for identifying the food item directly from the image 120. For example, if the identity of the food item cannot be determined with sufficient confidence from the image recognition of the food item itself, the user device 110 or backend server 300 may invoke block 420 to identify the food item via the surrounding food-related objects with or without images of the food item itself.

Block 420 includes sub-block 421, to identify a food container 130 in the image 120, sub-block 422 to identify a utensil 140 in the image 120, and sub-block 423 to identify secondary containers 150 in the image 120. In various embodiments, one or more sub-blocks of block 420 may not identify a respective container 130, utensil 140, or secondary container 150, which may provide the lack of an associated object as useful information in determining the identity of the food item in the image 120. For example, the presence of utensils 140 may indicate that the food item is not a sandwich (or other food typically eaten without utensils 140), but, in contrast, the lack of utensils 140 (i.e., a null utensil 140 being identified) may also indicate that the food item is more likely to be a food item typically eaten without utensils 140 (e.g., a sandwich) than if utensils 140 were identified in the image 120.

The image processing device, at each of the sub-blocks 421, 422, 423, may output a confidence score that an associated food-related object is present in the image 120. For example, at sub-block 421, the image processing device may output a confidence of X % that the container 130 is from provider A, Y % that the container is from provider B, Z % from provider C, etc. Similarly, at sub-block 422, the image processing device may output a confidence of X % that the utensil 140 is of type A, Y % that the container is of type B, Z % of type C, etc.

Various image recognition algorithms, including text/character recognition, may be performed in each of sub-blocks 421, 422, 423 in any order and with reference to the outputs of other sub-blocks 421, 422, 423. For example, the probability of identification of a utensil 140 as a pair of chopsticks (as opposed to a fork, straw skewer, etc.) in sub-block 422 may be greater in response to identifying a food container 130 in sub-block 421 as being associated with a restaurant known to serve food items consumed with chopsticks than if the food container 130 identified in sub-block 421 were identified with a restaurant not known to serve food items with chopsticks. In various embodiments, the user device 110 or backend server 300 may use image recognition algorithms that use sub-blocks 421, 422, 423 in addition to or instead of image recognition algorithms for identifying food items by the unique appearance of the food item alone.

At block 430, the user device 110 or backend server 300 identifies the food item in the image 120 based on the confidence of the food-related objects identified from the image 120 per block 420. The user device 110 or the backend server 300 may query the food recognition database 322 with an identity of the food container 130, utensil 140, and/or secondary container 150 to determine if one or more food items are associated with the identified food-related object. In response to determining that the food container 130, utensil 140, and/or secondary container 150 is present in the food recognition database 322 and is/are associated with a known food provider or food item, the food recognition database 322 returns identifiers for one or more food items or food providers associated with the food-related object.

A machine learning model 321 that associates various food items with recognized containers 130, utensils 140, and secondary containers 150 (and the food items contained therein) may determine a cluster of potential food items in the food recognition database 322 that may be found in the image 120 based on the identities of the objects identified per block 420 and the previously identified food items in the machine learning model 321 associated with the user who submitted the image 120. For example, when a container 130 having the distinctive shape and coloration associated with a fried chicken restaurant is identified in the image, and utensils 140 of a knife and fork are identified, a food item of a chicken cutlet may be identified from the image 120, as opposed to a sandwich, drumsticks or other food items consumed without utensils 140 offered by the identified restaurant or food items from other restaurants. In another example, an image 120 including a container 130 of a can may be identified as containing 355 mL of soda based on a known size of the can or sizing information on the can, and the logos and designs of the can.

Block 430 includes sub-block 431, to determine a confidence score for the food item included in the image 120. The candidate food item selected from the cluster of potential food items may be the potential food item with the highest confidence score of matching the food item in the image that satisfies a confidence threshold. The image processing device may include the individual confidences of the container 130, utensil 140, and secondary containers 150 present in the image 120 with a confidence of direct image detection of the food item from the image 120 to determine the food item that is best-believed to be in the image 120.

In various embodiments, the individual confidence scores produced per sub-blocks 421, 422, 423 may be weighted based on the dietary log to account for prior user history when determining the confidence score per sub-block 431. For example, if a first user consistently uses a fork-type utensil 140 to consume foods of every cuisine type, the identification of a utensil-type may be afforded a lower weight in determining a food item consumed by the first user than for a second user who matches a utensil-type to a cuisine type (e.g., chopsticks for Asian foods, forks for European foods). In another example, a user who consistently consumes food of various types from a single container (e.g., a plain paper lunch bag) may influence the image processing device to afford greater weight to the identification of a container 130 than a user who inconsistently consumes foods from various re-used containers 130 (e.g., a user frequently brings leftovers from restaurant A in containers supplied by restaurant B).

In embodiments that incorporate image recognition of the food items directly, the user device 110 or backend server 300 may use the image recognition of the containers 130, utensils 140, and secondary containers 150 to further improve the confidence in which a food item is directly identified in the image 120. For example, the direct identification of a food item from an image 120 with a confidence score of 0.74 of being chicken lo mien (a dish typically eaten with chopsticks) and a confidence score of 0.84 of being chicken fettucine (a dish typically eaten with a fork), may be adjusted to a confidence of 0.95 chicken lo mien and 0.02 of being chicken fettucine when the user device 110 or backend server 300 identifies utensils 140 of chop sticks in the image 120.

In some embodiments, the food item identified in the image 120 is a specific food item, while in other embodiments, the food item identified in the image 120 is a composite food. For example, a user may visit a restaurant that has several food items that may be similar in appearance. The user device 110 or backend server 300 may correctly identify the container 130, utensils 140, and secondary containers 150, but multiple food items may satisfy a confidence score. The machine learning model 321 may select one of the multiple food items to identify as being consumed by the user, or may select an average or aggregate value from the candidate food items. For example, a model may correctly identify the user as eating a curry from a particular establishment, but may be unable to determine which of the N curries served by the establishment that the user is eating. The model may select one of the N curries at random, based on prior selections in the dietary log for the user, or the relative confidences of the curries, or may select an aggregate food item of "curry" rather than "curry X", "curry Y", or "curry Z", and the nutritional values may be an unweighted or weighted average of the candidate food items.

At block 440, the user (optionally) verifies the identity of the food item. In some embodiments, the user device 110 or backend server 300 queries the user to confirm or reject the identified food item as the food item being consumed, to identify the food item being consumed, to confirm or reject the identity of a container 130, utensil 140, or secondary container 150 identified, or to identify a container 130, utensil 140, or secondary container 150. For example, the user device 110 may display a visual query and/or play an audio query of "Are you eating a bagel?" in response to identifying a baker's box (the container 130), a tub of cream cheese (a secondary container 150), and a knife (a utensil 140), to which the user may respond "yes" or "no". In another example, the user device 110 may display a visual query and/or play an audio query of "What are you eating?" in response to the machine learning model 321 not being able to identify a food item with a confidence score greater than a confidence score threshold, to which the user may reply with the identity of the food item. User device 110 shares the responses from the user with the machine learning model 321 for that user so that when presented with similar inputs (e.g., the same set of containers 130, utensils 140, and secondary containers 150), the machine learning model 321 will be more likely to return the correct result with a higher confidence.

At block 450, the user device 110 or backend server 300 adds the identified food item to the dietary log for the user. The identity of the food item identified in block 430 (or confirmed in block 440) is added, as are the nutritional information that correspond to the identified food item.

At block 460, the user device 110 or backend server 300 analyzes the dietary log to determine whether the identified food item triggers an alert threshold. In some embodiments, the identified food item triggers the alert threshold in response to the identity of the food item, such as, for example, when the food item or ingredient thereof is forbidden by a dietary plan set for the user. In other embodiments, the identified food item triggers the alert threshold in response to the aggregated nutrition profile exceeding a predefined limit for calories, foods of a certain category, micronutrients (e.g., vitamins and minerals), macronutrients (e.g., fats, sugars, cholesterol, proteins) consumed within a given time period. In response to determining that the food trend status has been triggered, method 400 proceeds to block 470. Otherwise, method 400 may then end.

At block 470, the user device 110 and/or backend server 300 generates an alert in response to the alert threshold being satisfied (per block 460). An alert may be transmitted to the user device 110 or to a third party device 350 (e.g., a cell phone of a doctor, parent, or concerned party) to signal the associated person that the user may be deviating from a prescribed diet. The alert may be sent as a page, a text message, a phone call, an email message, an in-application method, etc. depending on the capabilities of the user device 110 or to a third party device 350 to which the alert is addressed. Method 400 may then end.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the following, reference is made to embodiments presented in this disclosure. However, the scope of the present disclosure is not limited to specific described embodiments. Instead, any combination of the following features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access applications (e.g., machine learning model 321 for health trend tracking, a food recognition database 322) or related data available in the cloud. For example, the health monitor 221 could execute on a computing system in the cloud and aid in the tracking of health trends by the identification of food items from the food-related objects in a submitted image 120. In such a case, the health monitor 221 could identify food items for tracking health trends of a user and store images 120, dietary plans, and dietary logs at a storage location in the cloud. Doing so allows a user to access this information from any computing system attached to a network connected to the cloud (e.g., the Internet).

While the foregoing is directed to embodiments of the present invention, other and further embodiments of the invention may be devised without departing from the basic scope thereof, and the scope thereof is determined by the claims that follow.

What is claimed is:

1. A method, comprising:
   receiving an image captured from a user device that includes a first food item;
   identifying a food container for a second food item that is present in the image;
   identifying a utensil present in the image;
   determining, from a food recognition database, a cluster of food items corresponding to both the food container for the second food item and the utensil;
   selecting a candidate food item from the cluster based on a confidence score of the candidate food item matching the first food item; and
   adding the candidate food item to a dietary log associated with the user device.

2. The method of claim 1, wherein determining the cluster of food items from the food recognition database is done in response to the food recognition database returning a no-match result for an identity of the first food item via direct image recognition.

3. The method of claim 1, wherein the food container is identified based on a size and shape of the food container and at least one of:
   a color of the food container; and
   a logo present on the food container.

4. The method of claim 1, wherein the utensil is identified by distinguishing the utensil from between at least two of:
   a null utensil;
   a chopstick;
   a fork;
   a knife;
   a spoon; and
   a straw.

5. The method of claim 1, further comprising determining whether the candidate food item triggers an alert threshold based on at least one of:
   a medication included in the dietary log noted as conflicting with the candidate food item,
   a diet plan included in the dietary log; and
   in response to determining that the candidate food item triggers the alert threshold, transmitting an alert to the user device.

6. The method of claim 1, further comprising determining whether the first food item triggers an alert threshold based on a nutritional value taken in aggregate with earlier-consumed food items in a predefined time period exceeding a trend threshold; and
   in response to determining that the first food item triggers the alert threshold, transmitting an alert to the user device.

7. The method of claim 6, wherein the alert is transmitted to a third party device associated with one of:
   a doctor;
   a parent; and
   a nutritionist.

8. A system for health trend tracking, comprising:
   a processor; and
   a memory, including instructions that when executed by the processor enable the processor to:
   receive an image captured from a user device that includes a first food item;
   identify a food container for a second food item present in the image;
   identify a utensil present in the image;
   determine, from a food recognition database, a cluster of food items corresponding to both the food container for the second food item and the utensil;
   select a candidate food item from the cluster based on a confidence score of the candidate food item matching the first food item; and
   add the candidate food item to a dietary log associated with the user device.

9. The system of claim 8, wherein determining a cluster of food items from the food recognition database is done in response to the food recognition database returning a no-match result for an identity of the first food item via direct image recognition.

10. The system of claim 8, wherein the food container is identified based on a size and shape of the food container and at least one of:
    a color of the food container; and
    a logo present on the food container.

11. The system of claim 8, wherein the utensil is identified by distinguishing the utensil from between at least two of: as one of:
    a null utensil;
    a chopstick;

a fork;
a knife;
a spoon; and
a straw.

12. The system of claim 8, further comprising determining whether the candidate food item triggers an alert threshold based on at least one of:
   a medication included in the dietary log noted as conflicting with the candidate food item,
   a diet plan included in the dietary log; and
   in response to determining that the candidate food item triggers the alert threshold, transmitting an alert to the user device.

13. The system of claim 8, further comprising
   determining whether the first food item triggers an alert threshold based a
   nutritional value taken in aggregate with earlier-consumed food items in a
   predefined time period exceeding a trend threshold; and
   in response to determining that the first food item triggers the alert threshold, transmitting an alert to the user device.

14. The system of claim 13, wherein the alert is transmitted to a third party device associated with one of:
   a doctor;
   a parent; and
   a nutritionist.

15. A computer program product for health trend tracking, the computer program product comprising:
   a computer-readable storage medium having computer-readable program code embodied therewith, the computer-readable program code executable by one or more computer processors to:
      receive an image captured from a user device that includes a food item, a secondary food item, and a utensil;
      identify the secondary food item based on a food container for the secondary food item present in the image;
      identify the utensil present in the image;
      determine, from a food recognition database, a cluster of food items corresponding to both the secondary food item and the utensil;
      select a candidate food item from the cluster based on a confidence score of the candidate food item matching the food item; and
      add the candidate food item to a dietary log associated with the user device.

16. The computer program product of claim 15, wherein determining a cluster of food items from the food recognition database is done in response to the food recognition database returning a no-match result for an identity of the food item via direct image recognition.

17. The computer program product of claim 15, wherein the food container is identified based on a size and shape of the food container and at least one of:
   a color of the food container; and
   a logo present on the food container.

18. The computer program product of claim 15, further comprising determining whether the candidate food item triggers an alert threshold based on at least one of:
   a medication included in the dietary log noted as conflicting with the candidate food item,
   a diet plan included in the dietary log; and
   in response to determining that the candidate food item triggers the alert threshold, transmitting an alert to the user device.

19. The computer program product of claim 15, further comprising determining whether the food item triggers an alert threshold based on
   a nutritional value taken in aggregate with earlier-consumed food items in a predefined time period exceeding a trend threshold; and
   in response to determining that the food item triggers the alert threshold, transmitting an alert to the user device.

20. The computer program product of claim 19, wherein the alert is transmitted to a third party device associated with one of:
   a doctor;
   a parent; and
   a nutritionist.

* * * * *